United States Patent [19]

Yamaguchi et al.

[11] Patent Number: 4,692,554

[45] Date of Patent: Sep. 8, 1987

[54] PROCESS FOR PRODUCING 1,3-BIS(3-AMINOPHENOXY)BENZENE

[75] Inventors: Keizaburo Yamaguchi; Yukihiro Yoshikawa; Yoshimitsu Tanabe; Kenichi Sugimoto; Akihiro Yamaguchi, all of Tokyo, Japan

[73] Assignee: Mitsui Toatsu Chemicals, Inc., Tokyo, Japan

[21] Appl. No.: 638,732

[22] Filed: Aug. 7, 1984

[30] Foreign Application Priority Data

Oct. 18, 1983 [JP] Japan ............................... 58-193428
Dec. 6, 1983 [JP] Japan ............................... 58-229075
Dec. 6, 1983 [JP] Japan ............................... 58-229076

[51] Int. Cl.$^4$ .......................... C07C 41/09; C07C 93/14
[52] U.S. Cl. ..................................... 564/430; 564/412
[58] Field of Search ................ 564/430, 412; 528/127, 528/128

[56] References Cited

U.S. PATENT DOCUMENTS

| | | | |
|---|---|---|---|
| 3,879,349 | 4/1975 | Bilow et al. ......................... | 528/127 |
| 4,222,962 | 9/1980 | Pellegrini, Jr. ...................... | 564/430 |
| 4,469,893 | 9/1984 | Tang et al. ...................... | 564/430 X |
| 4,532,350 | 7/1985 | Cordier et al. ...................... | 564/412 |
| 4,539,428 | 9/1985 | Merrell et al. ....................... | 564/430 |

OTHER PUBLICATIONS

March, *Advanced Organic Chemistry, Reactions, Mechanisms and Structure*, 3rd Ed., pp. 584–587, 589, (1985).
Kirk–Othmer, *Encyclopedia of Chemical Technology*, Third Ed., vol. 9, John Wiley & Sons: New York, 1980, pp. 384–385.
Morrison et al, *Organic Chemistry*, Third Ed., Allyn and Bacon, Inc.: Boston, 1973, pp. 359–361, 556–558.
Theilheimer, *Synthetic Methods of Organic Chemistry*, vol. 1, (1942–44),p. 28; Interscience Pub'rs, 1948.

*Primary Examiner*—Charles F. Warren
*Assistant Examiner*—C. S. Greason
*Attorney, Agent, or Firm*—Jeffers, Hoffman & Niewyk

[57] ABSTRACT

A process for producing 1,3-bis(3-aminophenoxy)-benzenes which are very useful as a monomer for heat-resistant high molecular weight polymers is provided, which process comprises dehalogenating a bis(3-aminophenoxy)-halogenobenzene by its reduction, which compound is selected from the group consisting of 1,3-bis(3-aminophenoxy)-5-halogenobenzenes, 1,3-bis(3-aminophenoxy)-2,4-dihalogenobenzenes and 1,5-bis(3-aminophenoxy)-2,4-dihalogenobenzenes, these raw material compounds being respectively obtained by reacting a 1,3,5-trihalogenobenzene, a 1,2,3,4-tetrahalogenobenzene or a 1,2,4,5-tetrahalogenobenzene with 3-aminophenol in the presence of a dehydrohalogenating agent.

6 Claims, No Drawings

PROCESS FOR PRODUCING 1,3-BIS(3-AMINOPHENOXY)BENZENE

BACKGROUND OF THE INVENTION

This invention relates to a process for producing 1,3-bis(3-aminophenoxy)benzene.

1,3-Bis(3-aminophenoxy)benzene (hereinafter abbreviated to APB) is an important material which is used as a monomer for heat-resistant high molecular weight polymers, particularly as a raw material for polyamides and polyimides.

For example, an acetylene-terminated polyimide produced from APB, 3,3',4,4'-benzophenonetetracarboxylic acid dianhydride and 3-aminophenylacetylene has been known to be a polymer ranked as one of those having a highest heat resistance among polyimides (U.S. Pat. No. 3,845,018; U.S. Pat. No. 3,879,349).

As to processes for producing APB, a process of condensing resorcin with 1-bromo-3-nitrobenzene followed by reduction (German patent application laid-open No. 2,462,112) and a process of condensing 3-aminophenol with 1,3-dibromobenzene (W. Fin et al, Helv. Chim. Acta, 51, 971 (1968); U.S. Pat. No. 4,222,962) have been known.

In the case of the above reaction of resorcin with 1-bromo-3-nitrobenzene among the above processes for producing APB, resorcin is first treated with sodium methoxide in a large amount of benzene, followed by carrying out dehydration operation while recovering benzene by distillation to form resorcindisodium which is then reacted with 3-nitrobromobenzene in the presence of cuprous chloride in a large amount of pyridine solvent under argon stream to obtain 1,3-bis(3-nitrophenoxy)benzene (yield; 41%) which is then reduced with ferrous sulphate to obtain the objective compound.

Further according to the production process of condensing 3-aminophenol with 1,3-dibromobenzene, the both are reacted at 200°~280° C. in the presence of copper powder or reacted in the presence of cuprous chloride in a large amount of pyridine to produce the objective compound, but the yield is as low as 45~65%.

As described above, as to known processes for producing APB, ① a reaction solvent such as pyridine having a drawback of handling with respect of disagreeable smell is used in a large amount; further ② a dehydration solvent such as benzene is used in a large amount in order to inhibit side reactions such as hydrolysis; thus an operation of strict moisture removal is required; moreover ③ since a reaction promotor such as copper powder, cuprous chloride or the like is used, caution should be paid as to coloring, removal of copper ion, etc; still further ④ reaction is carried out in an inert gas; hence it is very difficult to commercially practice these processes in view of production operations, converting disposed materials into non-public-pollution materials, etc.

SUMMARY OF THE INVENTION

The object of the present invention is to provide a process for producing APB having overcome the above-mentioned drawbacks of the prior art, in a high purity and with a high yield.

The present invention resides in a process for producing APB which comprises dehalogenating a bis(3-aminophenoxy)-halogenobenzene selected from the group consisting of 1,3-bis(3-aminophenoxy)-5-halogenobenzenes, 1,3-bis(3-aminophenoxy)-2,4-dihalogenobenzenes and 1,5-bis(3-aminophenoxy)-2,4-dihalogenobenzenes, by its reduction.

DESCRIPTION OF PREFERRED EMBODIMENTS

The raw material 1,3-bis(3-aminophenoxy)-5-halogenobenzenes are obtained by subjecting a 1,3,5-trihalogenobenzene and 3-aminophenol to condensation reaction in the presence of a dehydrohalogenation agent.

Similarly, the raw materials 1,3-bis(3-aminophenoxy)-2,4-dihalogenobenzenes and 1,5-bis(3-aminophenoxy)-2,4-dihalogenobenzenes are obtained by subjecting a 1,2,3,4-tetrahalogenobenzene or a 1,2,4,5-tetrahalogenobenzene and 3-aminophenol to condensation reaction in the presence of a dehydrohalogenation agent.

This process is characterized in that the 1,2,3,4-tetrahalogenobenzenes or 1,2,4,5-tetrahalogenobenzenes both form 1,3-bis(3-aminophenoxy)-2,4-dihalogenobenzenes or 1,5-bis(3-aminophenoxy)-2,4-dihalogenobenzenes both capable of being dehalogenated. When a mixture of the above two kinds of the tetrahalogenobenzenes is used as raw materials for the condensation reaction, there is formed a mixture of 1,3-bis(3-aminophenoxy)-2,4-dihalogenobenzenes with 1,5-bis(3-aminophenoxy)-2,4-dihalogenobenzenes in a ratio corresponding to the mixing ratio of the above compounds. It is possible to lead either of the foregoing to APB.

According to the process of the present invention, bis(3-aminophenoxy)halogenobenzenes are subjected to catalytic reduction in the presence of a reduction catalyst in an organic solvent or reduced with formic acid and/or a salt of formic acid or hydrazine in the presence of Pd catalyst, to effect dehalogenation, whereby the objective APB is produced.

The halogen of the raw material bis(3-aminophenoxy) halogenobenzenes used in the process of the present invention is chlorine or bromine atom.

Examples of 1,3-bis(3-aminophenoxy)-5-halogenobenzenes are 1,3-bis(3-aminophenoxy)-5-chlorobenzene and 1,3-bis(3-aminophenoxy)-5-bromobenzene. These may be used alone or in admixture as a raw material for APB according to the process of the present invention, but commercially it is preferred to use cheap 1,3-bis(3-aminophenoxy)-5-chlorobenzene.

1,3-Bis(3-aminophenoxy)-5-halogenobenzenes are obtained by subjecting 1,3,5-trihalogenobenzenes and 3-aminophenol to condensation reaction in the presence of a dehydrohalogenation agent.

According to this process, copper compounds which are generally used as a reaction promotor in Ullmann reaction such as the above reaction of 1,3-dibromobenzene with 3-aminophenol are not used, and the condensation reaction readily proceeds under mild conditions by way of a simple operation of removing water content to obtain 1,3-bis(3-aminophenoxy) halogenobenzenes selectively and with a high yield. Thus, the compounds are dehalogenated by reduction without isolating and purifying them to obtain the objective compounds. This is the specific feature of the process.

Examples of 1,3,5-trihalogenobenzenes are 1,3,5-trichlorobenzene, 1,3-dichloro-5-bromobenzene, 1,3-dibromo-5-chlorobenzene and 1,3,5-tribromobenzene.

When 1,3,5-trichlorobenzene or 1,3-dichloro-5-bromobenzene is used as starting material, the condensation product is 1,3-bis(3-aminophenoxy)-5-chlorobenzene, and when 1,3-dibromo-5-chlorobenzene is used as starting material, the main condensation product is 1,3-bis(3-aminophenoxy)-5-chlorobenzene. When 1,3,5-tribromobenzene is used as starting material, the condensation product is 1,3-bis(3-aminophenoxy)-5-bromobenzene. The reaction is carried out using 3-aminophenol in an amount of 2 to 5 times by mol, preferably 2.1 to 3 times by mol the amount of 1,3,5-trihalogenobenzenes.

The dehydrohalogenation agent used is alkali metal hydroxides, carbonates, bicarbonates or alkoxides, and concrete examples thereof are potassium hydroxide, sodium hydroxide, lithium hydroxide, potassium carbonate, sodium carbonate, lithium carbonate, potassium bicarbonate, sodium bicarbonate, potassium ethoxide, potassium isopropoxide, sodium methoxide, sodium ethoxide, lithium ethoxide, etc. These may be used in a combination of two or more kinds thereof, not to mention their single use. The amount of these dehydrohalogenation agents used may be an equivalent amount or more to that of 3-aminophenol, preferably 1 to 1.5 equivalent amount thereto.

In the condensation reaction, a solvent may be used, and non-protonic polar solvents are preferably used. Examples of non-protonic polar solvents are N-methylformamide, N,N-dimethylformamide, N,N-dimethylacetamide, dimethyl sulfoxide, dimethyl sulfone, sulfolane, N-methylpyrrolidone, 1,3-dimethyl-2-imidazolidinone, phosphoric acid hexamethyltriamide, etc. The amount of these solvents used has no particular limitation, but usually 1 to 10 times by weight the amount of the raw material may be sufficient.

The above 3-aminophenol, dehydrohalogenation agent and solvent may be fed into a reactor, followed by converting 3-aminophenol into its alkali metal salt and then adding a 1,3,5-trihalogenobenzene to react them, or alternatively the whole raw materials including a 1,3,5-trihalogenobenzene may be added at the same time, followed by raising the temperature as they are, to react them. For removing water formed in the reaction system, there is employed a method of passing nitrogen gas or the like and thereby gradually discharging water to the outside of the system during the reaction, but generally there is often employed a method of removing it to the outside of the system through azeotropy using a small amount of benzene, toluene, xylene, chlorobenzene or the like.

The reaction is usually carried out at a temperature in the range of 120° to 240° C., preferably 140° to 200° C. After completion of the reaction, the reaction liquid is discharged into water or the like after concentration or as it is, to obtain the objective product.

Further, as the raw material, 1,3-bis(3-aminophenoxy)-2,4-dihalogenobenzenes or 1,5-bis(3-aminophenoxy)-2,4-dihalogenobenzenes, usually, for example, 1,3-bis(3-aminophenoxy)-2,4-dichlorobenzene or 1,5-bis(3-aminophenoxy)-2,4-dichlorobenzene is often used.

The above bis(3-aminophenoxy) dihalogenobenzenes are obtained by subjecting tetrahalogenobenzenes and 3-aminophenol to condensation reaction in the presence of a dehydrohalogenation agent, preferably in an organic solvent. In this condensation reaction, two halogen atoms at meta-position are each substituted by 3-aminophenoxy group to give 1,3-bis(3-aminophenoxy)-2,4-dihalogenobenzenes in the case of 1,2,3,4-tetrahalogenobenzenes, and 1,5-bis(3-aminophenoxy)-2,4-dihalogenobenzenes in the case of 1,2,4,5-tetrahalogenobenzenes. When either of these are dehalogenated by reduction, they can be led to the objective APB. Further, when mixtures of 1,2,3,4-tetrahalogenobenzenes with 1,2,4,5-tetrahalogenobenzenes are used, mixtures of condensation products in a ratio corresponding to the mixing ratio of the above compounds are obtained and any of these mixtures can be led to APB.

3-Aminophenol is used in an amount of 2 to 5 times by mol, preferably 2.1 to 3 times by mol the amount of the tetrahalogenobenzenes.

When the dehydrohalogenation agent, reaction solvent, reaction conditions, etc. are employed in the same manner as in the case of 1,3,5-trihalogenobenzenes, it is possible to obtain 1,3-bis(3-aminophenoxy)-2,4-dihalogenobenzenes or 1,5-bis(3-aminophenoxy)-2,4-dihalogenobenzenes.

In the process of the present invention, the dehalogenation reaction is usually carried out either (i) by dehalogenation by catalytic reduction of (ii) by dehalogenation by the use of a reducing agent, both in the presence of a reducing catalyst in a solvent.

The dehalogenation may be carried out using isolated 1,3-bis(3-aminophenoxy)-5-halogenobenzenes, 1,3-bis(3-aminophenoxy)-2,4-dihalogenobenzenes or 1,5-bis(3-aminophenoxy)-2,4-dihalogenobenzenes, or in succession to the above condensation reaction without isolating bis(3-aminophenoxy)halogenobenzenes from the reaction mixture obtained by the condensation reaction.

In the above reduction step, the dehydrohalogenation agent may be either present or absent. The reaction readily proceeds in either case to make it possible to produce the objective product in a high purity, with a good yield and without any byproduct. Thus, the process has no drawback of low yield, necessity of complicated operations in the reaction and purification, etc. as seen in conventional processes; hence it is suitable for a commercial production process.

As the reducing catalyst used in the above process (i), it is possible to use metal catalysts which have generally been used for catalytic reduction, such as Ni, Pd, Pt, Rh, Ru, Co, Cu, etc. Commercially, Pd catalyst is preferably used. These catalysts may be used in the form of metal, but usually may be used in the form of these metals supported on a carrier such as active carbon, barium sulfate, silica gel, alumina, etc., or may be used in the form of Raney catalyst in the case of Ni, Co, Cu, etc. The amount of the catalyst used is in the range of 0.01 to 10% by weight in terms of metal based on bis(3-aminophenoxy)halogenobenzenes, and usually in the range of 1 to 10% by weight in the case where it is used in the form of metal, while in the range of 0.05 to 1% by weight in the case where metal is supported on a carrier.

In this dehalogenation reaction, hydrogen halide is formed by the catalytic reduction reaction. In order to seize this hydrogen halide, a dehydrohalogenation agent may be used.

As the dehydrohalogenation agent, oxides, hydroxides, carbonates, bicarbonates and lower fatty acid salts of alkali metals or alkaline earth metals, ammonia or usual organic amines may be used. Concrete examples thereof are calcium carbonate, sodium hydroxide, magnesium oxide, ammonium bicarbonate, calcium oxide, lithium hydroxide, barium hydroxide, potassium carbonate, potassium hydroxide, sodium acetate, potassium propionate, ammonia, triethylamine, tri-n-butylamine, triethanolamine, pyridine, N-methyl-morpholine, etc.

These bases may be used in admixture of two or more kinds, if necessary.

The amount of the bases used may be an equivalent amount or more based on bis(3-aminophenoxy)-halogenobenzenes, and usually 1 to 3 equivalents are added.

The reaction solvent in this reaction has no particular limitation so long as they are inert to the reaction. Its examples are alcohols such as methanol, ethanol, isopropanol, glycols such as ethylene glycol, propylene glycol, ethers such as ether, dioxane, tetrahydrofuran, methylcellosolve, aliphatic hydrocarbons such as hexane, cyclohexane, aromatic hydrocarbons such as benzene, toluene, esters such as ethyl acetate, butyl acetate, halogenated hydrocarbons such as chloroform, 1,2-dichloroethane, 1,1,2-trichloroethane, N,N'-dimethylformamide, N-methylpyrrolidone, 1,3-dimethyl-2-imidazolidinone, water, etc. As for the amount of the solvent used, an amount enough to suspend or dissolve bis(3-aminophenoxy)halogenobenzenes may be sufficient and the amount has no particular limitation, but usually 0.5 to 10 times by weight the amount of bis(3-aminophenoxy)halogenobenzenes may be sufficient.

As for a general embodiment of this reaction, a catalyst is added to bis(3-aminophenoxy)halogenobenzenes dissolved or suspended in a solvent, followed by carrying out, as it is, catalytic reduction reaction at a definite temperature to effect dehalogenation.

On the other hand, in the case of use of a dehydrohalogenation agent, too, catalytic reduction reaction may be similarly carried out, but in this case, there may be employed either a method of adding a dehydrohalogenation agent in advance to effect reaction, or a method of successively adding the agent during the reaction.

The temperature of this reaction has no particular limitation, but generally a range of 20° to 200° C., particularly 20° to 100° C., is preferable. Further, the reaction pressure may be usually in the range of ordinary pressures to 50 Kg/cm$^2$. The end point of the reaction may be determined by measuring the amount of hydrogen absorbed.

After the reaction, there may be employed a method wherein when the reaction product is in dissolved state, it is filtered to remove catalyst, etc. followed by concentration, dilution or the like to deposit it in the form of crystals, or a mineral acid is added to deposit it in the form of its mineral acid salt, followed by neutralization to obtain the objective compound, and the like method. Further, when it is in deposited state, it may be melted on heating, followed by filtration while hot to remove catalyst, and cooling to obtain deposited crystals of the objective compound.

Next, as to the above process (ii) using a reducing agent, reduction is carried out using formic acid and/or a formic acid salt or hydrazine in the presence of Pd catalyst, to effect dehalogenation. According to this process, similarly the reaction readily proceeds and it is possible to produce the objective compound with a high yield and without any byproduct.

The reducing agent used in this process of the present invention is formic acid, formic acid salts or hydrazine.

Examples of the above reducing agent are alkali metal salts of formic acid such as sodium formate, potassium formate, organic amine salts such as ethylamine formate, ammonium formate, etc. and these salts may be used alone or in admixture with formic acid.

Pd catalyst may be used in the form of metal, but usually is used in the form of Pd supported on a carrier. Examples of the catalyst are Pd black, Pd-active carbon, Pd-alumina, Pd-barium sulfate, etc.

The amount of the catalyst used is in the range of 0.01 to 10% by weight based on the raw material, bis(3-aminophenoxy)halogenobenzenes.

The reaction solvent has no particular limitation so long as it is inert to the reaction, but usually solvents miscible with water are used. Examples of the solvent are alcohols such as methanol, ethanol, isopropanol, glycols such as ethylene glycol, propylene glycol, ethers such as tetrahydrofuran, dioxane, methyl cellosolve, and non-protonic polar solvents such as N,N'-dimethylformamide, N-methyl-pyrrolidone. As to the amount of the solvent used, an amount enough to suspend or completely dissolve the raw material may be sufficient and it has no particular limitation, but usually 0.5 to 1.0 times by weight the amount of the raw material may be sufficient.

The reaction temperature has no particular limitation, but usually it is in the range of 20° to 130° C.

In carrying out the present invention, generally, formic acid and/or a formic acid salt or hydrazine and a catalyst are added to a raw material dissolved or suspended in a solvent, followed by reacting them at a definite temperature with stirring.

In either case, the reaction proceeds smoothly to make it possible to produce the objective APB. The advance of the reaction can be traced by thin-layer chromatography or high rate liquid chromatography.

The reaction liquid obtained according to the above process may be filtered while hot to remove catalyst, followed by concentration or dilution with water to deposit crystals, or a mineral acid may be added to deposit crystals in the form of a mineral acid salt.

The present invention will be described in more details by way of the following Examples.

EXAMPLE 1

Into a 2 l flask equipped with a stirrer and a water separator were fed 3-aminophenol (120 g, 1.1 mol), granular potassium hydroxide (purity 86%, 75 g, 1.15 mol), 1,3-dimethyl-2-imidazolidinone (hereinafter abbreviated to DMI) (500 ml) and xylene (50 ml), followed by raising the temperature while passing nitrogen with stirring to remove the water content in the reaction system under reflux of xylene by means of the water separator. The amount of water distilled off adds 20.5 ml.

Next, a solution of DMI (250 ml) and 1,3,5-trichlorobenzene (9.1 g, 0.5 mol) was added over one hour, followed by keeping the mixture at 145°~150° C. for 5 hours while distilling off xylene in the system. The temperature was then raised up to 170°~180° C. to carry out reaction for 18 hours.

Just after completion of the reaction, the solvent DMI was distilled off under a reduced pressure of 50~70 mmHg by means of an aspirator, and recovered. The amount of DMI recovered was 690 ml.

The distillation residue was fed into water (1.5 l) with vigorous stirring to separate a brown oily substance as a lower layer. This brown oily substance was raw 1,3-bis(3-aminophenoxy)-5-chlorobenzene, and its purity according to high rate liquid chromatography was 92.3%.

To the brown oily substance separated after still standing and decantation was added 6N-HCl aqueous solution (520 g, 2.5 mols), followed by dissolving it on heating, and then allowing the solution to cool to deposit 1,3-bis(3-aminophenoxy)-5-chlorobenzene hydrochloride, which was then filtered, washed with 10% aqueous solution of NaCl and dried to give a yield of 174.4 g (87.3%). The 1,3-bis(3-aminophenoxy)-5-chlorobenzene hydrochloride was recrystallized from isopropanol having a water content of 2% to obtain a pure product of white acicular crystals. M.P.: 268°~272° C. Results of its elemental analysis were as follows:

| Elemental analysis ($C_{18}H_{17}N_2O_2Cl_3$) | | | | |
|---|---|---|---|---|
| | C | H | N | Cl |
| Calculated value (%) | 54.09 | 4.29 | 7.01 | 26.61 |
| Observed value (%) | 53.92 | 4.34 | 7.0 | 26.59 |

Into a glass closed vessel was then fed the above 1,3-bis(3-aminophenoxy)-5-chlorobenzene hydrochloride (4 g, 0.01 mol), granular sodium hydroxide (purity 96%, 1.25 g, 0.03 mol), 5% Pd-C catalyst (0.08 g) and methanol (20 ml), followed by introducing hydrogen with vigorous stirring. Reaction was carried out at 25°~30° C. for 3 hours to absorb hydrogen (220 ml). No more absorption was observed; thus the reaction was completed. Successively, the reaction liquid was filtered to remove catalyst, etc., and conc. hydrochloric acid (20 ml) was added to the solution to deposit white, acicular crystals of 1,3-bis(3-aminophenoxy)benzene (APB) hydrochloride, followed by filtering, washing with isopropanol and drying. Yield: 3.5 g (95.9% based on 1,3-bis(3-aminophenoxy)-5-chlorobenzene hydrochloride).

Further, this APB hydrochloride was dissolved in water and neutralized with dilute aqueous ammonia to deposit white crystals, followed by filtering, water-washing and drying to obtain APB. Purity according to high rate liquid chromatography: 98.2%. This APB was recrystallized from isopropanol to obtain a pure product in the form of white, acicular crystals. M.P.: 105°~107° C. The elemental analysis values were as follows:

| Elemental analysis ($C_{18}H_{16}N_2O_2$) | | | |
|---|---|---|---|
| | C | H | N |
| Calculated value (%) | 73.95 | 5.52 | 9.58 |
| Observed value (%) | 73.88 | 5.7 | 9.51 |

EXAMPLE 2

3-Aminophenol (12 g, 0.11 mol), granular sodium hydroxide (purity 96%, 4.6 g, 0.11 mol), toluene (10 ml) and DMI (50 ml) were fed into the same apparatus as in Example 1, followed by raising the temperature while passing nitrogen with stirring to remove the water content in the reaction system under reflux of toluene by means of the water separator. DMI (50 ml) and 1,3,5-tribromobenzene (15.7 g, 0.05 mol) were then added, followed by reacting them at a temperature of 150° to 160° C. for 20 hours while distilling off toluene in the system.

The reaction mixture was then treated in the same manner as in Example 1 to obtain 1,3-bis(3-aminophenol)-5-bromobenzene hydrochloride, which was recrystallized from isopropanol having a water content of 2%, followed by dissolving it in water and neutralizing with dilute aqueous ammonia to liberate slightly brown, oily 1,3-bis(3-aminophenoxy)-5-bromobenzene, which was then extracted with ether, followed by vacuum drying to obtain slightly brown, oily 1,3-bis(3-aminophenoxy)-5-bromobenzene.

While this substance was used in the subsequent reaction, it was separately stored in a cold place to form crystals. M.P.: 68°~69° C. The elemental analysis values were as follows:

| Elemental analysis ($C_{18}H_{15}N_2O_2Br$) | | | | |
|---|---|---|---|---|
| | C | H | N | Br |
| Calculated value (%) | 58.24 | 4.07 | 7.55 | 21.53 |
| Observed value (%) | 58.09 | 4.18 | 7.48 | 21.45 |

Next, the above slightly brown, oily 1,3-bis(3-aminophenoxy)-5-bromobenzene (3.7 g, 0.01 mol), granular potassium hydroxide (purity 86%, 0.65 g, 0.01 mol), 5% Pd-C catalyst (0.1 g) and isopropanol (10 ml) were fed into a glass closed vessel and hydrogen was introduced with vigorous stirring. Reaction was carried out at 50°~60° C. for 2 hours to absorb hydrogen (228 ml). The reaction liquid was then filtered while hot at the same temperature as above, followed by adding warm water (10 ml) and allowing the mixture to cool, to deposit white, acicular APB, which was filtered, water-washed and dried to obtain the objective compound (2.81 g) (yield: 96.2% based on 1,3-bis(3-aminophenoxy)-5-bromobenzene). Purity: 98.9% according to high rate liquid chromatography. M.P.: 103°~106° C. The elemental analysis values were as follows:

| Elemental analysis ($C_{18}H_{16}N_2O_2$) | | | |
|---|---|---|---|
| | C | H | N |
| Calculated value (%) | 73.95 | 5.52 | 9.58 |
| Observed value (%) | 73.62 | 5.58 | 9.24 |

EXAMPLE 3

3-Aminophenol (12 g, 0.1 mol), 1,3-dibromo-5-chlorobenzene (13.5 g, 0.05 mol), potassium carbonate (10.4 g, 0.075 mol) and dimethylsulfoxide (100 ml) were fed into a flask equipped with a stirrer, to react them at 150°~170° C. for 24 hours, while passing nitrogen with stirring. Subsequent treatment was carried out in the same manner as in Example 1 to obtain a 1,3-bis(3-aminophenoxy)-5-halogenobenzene hydrochloride.

After its neutralization, analysis according to high rate liquid chromatography indicated that it was a mixture of 1,3-bis(3-aminophenoxy)-5-chlorobenzene with 1,3-bis(3-aminophenoxy)-5-bromobenzene in a proportion of 93:7.

This 1,3-bis(3-aminophenoxy)-5-halogenobenzene hydrochloride as a mixture of chloro-substance with bromo-substance was then subjected to reduction reaction and post-treatment under the same conditions as in Example 1 to obtain the objective APB. The yield as calculated from the composition ration of the raw materials was 93%.

EXAMPLE 4

1,3-Bis(3-aminophenoxy)-5-chlorobenzene hydrochloride obtained in Example 1 was dissolved in water and neutralized with dilute aqueous ammonia to liberate slightly brown, oily 1,3-bis(3-aminophenoxy)-5-chlorobenzene, which was extracted with ether, followed by drying in vacuo to obtain slightly brown, oily 1,3-bis(3-aminophenoxy)-5-chlorobenzene.

While the thus obtained was then subjected to dehalogenation, it was separately allowed to stand in a cold place to obtain crystals. M.P.: 72°~73° C. The values of elemental analysis were as follows:

| Elemental analysis ($C_{18}H_{15}N_2O_2Cl$) | | | |
| --- | --- | --- | --- |
| C | H | N | Cl |
| Calculated value (%) 66.16 | 4.63 | 8.57 | 10.85 |
| Observed value (%) 66.00 | 4.82 | 8.39 | 10.78 |

The above slightly brown, oily 1,3-bis(3-aminophenoxy)-5-chlorobenzene (3.3 g, 0.01 mol), 5% Pd-C catalyst (0.15 g) and 30% aqueous solution of dioxane were fed into a glass closed vessel and hydrogen was introduced with vigorous stirring. Reaction was carried out at 70°~80° C. for 3 hours to absorb hydrogen (212 ml). The reaction liquid was then filtered to remove the catalyst, neutralized with dilute aqueous ammonia and allowed to stand to deposit white, acicular crystals, followed by filtering, water-washing and drying to obtain the objective APB (2.75 g) (yield: 94.2% based on 1,3-bis(3-aminophenoxy)-5-chlorobenzene). M.P.: 103°~106° C.

EXAMPLE 5-8

Reaction was carried out as in Example 1 except that the dehydrohalogenation agent and the solvent at the time of reduction were varied as shown in Table 1, to obtain the objective APB. The dehydrohalogenation agents and the solvents used and the yields of APB (based on 1,3-bis(3-aminophenoxy)-5-chlorobenzene hydrochloride) are shown in Table 1.

TABLE 1

| No. of Example | Dehydrohalogenation agent | Solvent | Yield (%) |
| --- | --- | --- | --- |
| 5 | Potassium carbonate | Methanol | 91.6 |
| 6 | Triethylamine | Tetrahydrofuran | 89.1 |
| 7 | Sodium acetate | Ethyl acetate | 84.4 |
| 8 | Magnesium oxide | Methanol | 94.9 |

EXAMPLE 9

Slightly brown, oily 1,3-bis(3-aminophenoxy)-5-chlorobenzene (9.8 g, 0.03 mol), 10% Pt-C (0.2 g), 30% aqueous ammonia (3.4 g, 0.06 mol) and benzene (75 ml) were fed into an autoclave and hydrogen was introduced with vigorous stirring to keep the pressure at 5~7 Kg/cm². Reaction was carried out at an inner temperature of 40°~50° C. for 6.5 hours, followed by filtering to remove the catalyst, concentrating the reaction liquid and allowing to stand to deposit white, prismatic crystals, which were filtered and dried to obtain the objective APB. Yield: 6.85 g, 78.2% based on 1,3-bis(3-aminophenoxy)-5-chlorobenzene, M.P.: 104°~106.5° C.

EXAMPLE 10

Example 9 was repeated except that calcium hydroxide was used as the dehydrochlorination agent, 1,1,2-trichloroethane, as the solvent, and Raney nickel, as the catalyst, to obtain the objective APB (yield: 76.6% based on 1,3-bis(3-aminophenoxy)-5-chlorobenzene).

EXAMPLE 11

Condensation reaction was carried out in all the same manner as in Example 1, followed by filtering the reaction liquid to remove deposited potassium chloride. The reaction liquid after the filtration was introduced into a 2 l glass closed vessel. 5% Pd-C (4.9 g) and 30% aqueous solution of potassium hydroxide (100 g, 0.6 mol) were added and hydrogen was introduced with vigorous stirring. Reaction was carried out at an inner temperature of 30°~35° C. for 8 hours to absorb hydrogen (11.05 l). No more absorption was observed; thus the reaction was completed. The reaction liquid was then filtered to remove the catalyst, etc., followed by concentration under reduced pressure to recover the solvent DMI (the amount of DMI recovered; 670 ml). Warm water (1.5 l) was added to the residue after the concentration, followed by stirring, still standing and removing water of the upper layer by decantation. A tarry material of the lower layer was the objective APB. The purity according to high rate liquid chromatography was 93.6%. This tarry material was dissolved on heating in isopropanol (350 ml) and active carbon (3 g) was added, followed by filtering while hot, and allowing the filtrate to cool to deposite white, acicular crystals, which were then filtered and dried to obtain the objective product. Yield: 117.2 g (overall yield: 80.2%). M.P.: 103°~106° C.

EXAMPLE 12

Condensation reaction was carried out in all the same manner as in Example 1, followed by recovering DMI, dissolving a tarry substance as the residue in isopropanol (350 ml) and removing an insoluble matter by filtration.

The filtrate was fed into a 1 l glass closed vessel, 5% Pd-C (3.2 g) and granular sodium hydroxide (purity 96%, 21 g, 0.5 mol) were added and hydrogen was introduced with vigorous stirring. Reaction was carried out at a inner temperature of 50°~60° C. for 5 hours to absorb hydrogen (11.1l). No more absorption was observed; thus the reaction was completed. Just thereafter, catalyst, etc. were removed by filtering while hot, followed by allowing to cool to deposit white, acicular crystals, which were then filtered and dried to obtain the objective APB. Yield: 121.8 g (overall yield: 83.3%).

EXAMPLE 13

Into a glass vessel equipped with a thermometer, a reflux condenser and a stirrer were fed 1,3-bis(3-aminophenoxy)-5-chlorobenzene (8.2 g, 0.025 mol), 5% Pd-C (made by Japan Engelhardt Co.) (0.25 g), sodium formate (4.3 g, 0.063 mol) and 60% aqueous solution of isopropanol (50 ml), and reaction was carried out under reflux with stirring for 5 hours. After completion of the reaction, the catalyst was removed by filtering while hot, followed by cooling to deposit colorless, prismatic crystals, which were filtered and dried to obtain 1,3-bis(3-aminophenoxy)benzene (6.6 g, yield 90.3%). The purity according to high rate liquid chromatography was 99%. M.P.: 105°~107° C.

| Elemental analysis ($C_{18}H_{16}N_2O_2$) | | |
| --- | --- | --- |
| C | H | N |
| Calculated value (%) 73.95 | 5.52 | 9.58 |
| Observed value (%) 73.76 | 5.58 | 9.36 |

EXAMPLE 14

Into the same apparatus as in Example 13 were fed 1,3-bis(3-aminophenoxy)-5-bromobenzene (9.3 g, 0.025 mol), 5% Pd-C (0.2 g), hydrazine hydrate (3.8 g, 0.076 mol) and 50% aqueous solution of methanol (50 ml), and reaction was carried out under reflux with stirring for 5 hours. The subsequent operations were carried out in the same manner as in Example 13 to obtain the objective product (purity according to high rate liquid chromatography: 98.8%, yield: 6.9 g, 94.4%). M.P.: 105°~108° C.

EXAMPLES 15-18

Reaction was carried out in the same manner as in Example 13 except that 1,3-bis(3-aminophenoxy)-5-chlorobenzene was used as raw material and the solvent and the reducing agent were varied as shown in Table 2, to obtain the objective 1,3-bis(3-aminophenoxy)benzene. The solvents and the reducing agents used and the yields of the objective product are shown in Table 2.

TABLE 2

| No. of Example | Reducing agent (mol ratio) | Solvent | Yield (%) |
|---|---|---|---|
| 15 | Hydrazine hydrate (3) | 50% aq. solution of dioxane | 87.7 |
| 16 | Potassium formate (2.5) | 40% aq. solution of methyl cellosolve | 90.2 |
| 17 | Formic acid + triethylamine (3) | 60% aq. solution of isopropanol | 82.9 |
| 18 | Formic acid (6) | 40% aq. solution of dimethylformamide | 74.0 | reaction system by means of the water separator under reflux of toluene.

Next, a solution of dimethyl sulfoxide (25 ml) and 1,2,4,5-tetrachlorobenzene (10.8 g, 0.05 mol) was added over one hour, followed by raising the temperature while distilling off toluene in the system, and reacting them at 155°~160° C. for 5 hours.

Just after completion of the reaction, the solvent dimethyl sulfoxide was distilled off for recovery under a reduced pressure of 50~70 mmHg by means of an aspirator, followed by adding methanol (75 mm) to this reaction composition to dissolve it therein, adding active carbon (0.5 g), filtering and then introducing the filtrate together with 5% Pd-C catalyst (made by Japan Engelhardt Co.) (0.5 g) and 28% aqueous ammonia (9.1 g, 0.15 mol) into a glass closed vessel, just thereafter introducing hydrogen with vigorous stirring to carry out catalytic reduction reaction. Reaction was carried out at a reaction temperature of 25°~30° C. for 8 hours to absorb hydrogen (2150 ml). No more absorption was observed; thus the reaction was completed.

Successively the reaction liquid was filtered to remove the catalyst, etc. and concentrated to deposit pale brown crystals, followed by filtering, washing and drying to obtain raw APB. Yield: 12.2 g (83.5%).

This raw APB was recrystallized from isopropanol to obtain a pure product of colorless, prismatic crystals. M.P.: 106°~107° C. The values of elemental analysis were as follows:

| Elemental analysis ($C_{18}H_{16}N_2O_2$) | | | |
|---|---|---|---|
| | C | H | N |
| Calculated value (%) | 73.95 | 5.52 | 9.58 |
| Observed value (%) | 73.79 | 5.59 | 9.51 |

EXAMPLES 20-22

Example 19 was repeated except that the raw material, dehydrochlorination agent and solvent in the condensation reaction and the dehydrochlorination agent, catalyst and solvent in the catalytic reduction reaction were varied, to obtain the objective APB. The results are shown in Table 3.

TABLE 3

| No. of Example | Condensation reaction | | | Reduction reaction | | | APB yield (%) | Remark |
|---|---|---|---|---|---|---|---|---|
| | Raw material | Dehydro-chlorination agent | Solvent | Catalyst | Dehydro-chlorination agent | Solvent | | |
| 20 | 1,2,3,4-TCB (*) | Sodium methoxide | 1,3-dimethyl-2-imidazolidinone | 5% Pd—C | Sodium hydroxide | Methyl cellosolve | 78.6 | |
| 21 | 1,2,3,4-TCB (*) | Sodium hydroxide | N—methyl-pyrrolidone | 10% Pt—C | Triethyl-amine | Dioxane | 67.5 | Reduction under pressure (10~20 Kg/cm²) |
| 22 | 1,2,4,5-TCB (*) | Potassium carbonate | N,N—dimethyl-formamide | Raney Ni | Triethyl-amine | Ethanol | 49 | Reduction under pressure (30~35 Kg/cm²) |

(*) TCB: abbreviation of tetrachlorobenzene

EXAMPLE 19

Into a 200 ml flask equipped with a stirrer and a water separator were fed 3-aminophenol (12.0 g, 0.11 mol), granular potassium hydroxide (purity 86%, 7.5 g, 0.115 mol), dimethyl sulfoxide (50 ml) and toluene (5 ml), followed by raising the temperature while passing nitrogen with stirring and removing the water content in the

EXAMPLE 23

3-Aminophenol (12.0 g, 0.11 mol), granular sodium hydroxide (purity 96%, 4.6 g, 0.11 mol), benzene (10 ml) and N-methylpyrrolidone (50 ml) were fed into the same apparatus as in Example 19, followed by raising the temperature while passing nitrogen with stirring to remove the water content in the reaction system under reflux of benzene by means of a water separator. A solution of N-methylpyrrolidone (50 ml) and 1,2,3,4-tetrachlorobenzene (10.8 g, 0.05 mol) was then added, followed by raising the temperature and reacting them at 140°~160° C. for 6.5 hours. Just after completion of the reaction, the solvent N-methylpyrrolidone was distilled off for recovery under a reduced pressure of 50~70 mmHg by means of an aspirator. To this reaction composition were fed 60% aqueous solution of isopropanol (75 ml) and 5% Pd-C catalyst (0.7 g), followed by dropwise adding hydrazine (15 g, 0.3 mol) under reflux over one hour and successively reacting them under reflux for 5 hours. After completion of the reaction, the reaction liquid was filtered while hot to remove the catalyst, etc. and allowed to cool to deposit pale brown crystals, which were then filtered, washed and dried to obtain raw APB. Yield: 12 g (82.1%).

This raw APB was recrystallized from isopropanol to obtain a pure product of colorless, prismatic crystals. M.P.: 106°~107° C. The values of elemental analysis was as follows:

| Elemental analysis ($C_{18}H_{16}N_2O_2$) | | | |
|---|---|---|---|
| | C | H | N |
| Calculated value (%) | 73.95 | 5.52 | 9.58 |
| Observed value (%) | 73.99 | 5.69 | 9.42 |

EXAMPLE 24

3-Aminophenol (12.0 g, 0.11 mol), 1,2,4,5-tetrachlorobezene (10.8 g, 0.05 mol), potassium carbonate powder (15.2 g, 0.11 mol), benzene (10 ml) and N,N'-dimethylformamide (100 ml) were fed into the same apparatus as in Example 19, followed by raising the temperature while passing nitrogen to azeotropically distill off the water content in the system together with benzene, successively raising the temperature and reacting them under reflux at the boiling point of N,N'-dimethylformamide for 8 hours.

After completion of the reaction, insoluble inorganic salt was filtered off, followed by adding 86% formic acid (10.7 g, 0.2 mol) and 10% Pd-C (0.3 g) and carrying out reduction reaction at 50°~60° C. for 15 hours with stirring. After completion of the reaction, the reaction liquid was filtered to remove the catalyst, etc., and fed into water (one l to separate raw APB in the form of a tarry product, which was then dissolved on heating in 6N-hydrochloric acid aqueous solution (40 g) and allowed to cool, to deposit APB hydrochloride of pale brown, acicular crystals, which were filtered, washed with isopropanol and dried. Yield: 12.6 g (68.9%).

This product was recrystallized from a water-containing isopropanol to obtain pure APB hydrochloride of white, acicular crystals, M.P.: 106°–107° C. The values of elemental analysis were as follows:

| Elemental analysis ($C_{18}H_{18}N_2O_2Cl_2$) | | | | |
|---|---|---|---|---|
| | C | H | N | Cl |
| Calculated value (%) | 59.19 | 4.97 | 7.67 | 19.41 |
| Observed value (%) | 59.02 | 5.03 | 7.59 | 19.62 |

EXAMPLE 25

Example 23 was repeated except that hydrazine was replaced by sodium formate, to obtain the objective APB.

What is claim is:

1. A process for producing 1,3-bis(3-aminophenoxy) benzenes which comprises reacting a halogenobenzene selected from the group consisting of 1,3,5-trihalogenobenzenes, 1,2,3,4-tetrahalogenobenzenes and 1,2,4,5-tetrahalogenobenzenes with 3-aminophenol in the presence of a dehydrohalogenating agent in an aprotic polar solvent and in the absence of an Ullmann reaction promotor to obtain 1,3-bis(3-aminophenoxy)-5-halogenobenzen, 1,3-bis(3-aminophenoxy)-2,4-dihalogenobenzen or 1,5-bis(3-aminophenoxy)-2,4-dihalogenobenzen and dehalogenating the resulting bis(3-aminophenoxy) halobenzene by its reduction.

2. A process according to claim 1 wherein said reduction is catalytic reduction.

3. A process according to claim 1 wherein said reduction is carried out using formic acid and/or a salt of formic acid in the presence of a reducing catalyst.

4. A process according to claim 1 wherein said 1,3-bis(3-aminophenoxy)-5-halogenobenzenes are a reaction product obtained by reacting a 1,3,5-trihalogenobenzene with 3-aminophenol in the presence of a dehydrohalogenating agent in an aprotic polar solvent and in the absence of an Ullmann reaction promotor.

5. A process according to claim 1 wherein said 1,3-bis(3-aminophenoxy)-2,4-dihalogenobenzenes are a reaction product obtained by reacting a 1,2,3,4-tetrahalogenobenzene with 3-aminophenol in the presence of a dehydrohalogenating agent in an aprotic polar solvent and in the absence of an Ullmann reaction promotor.

6. A process according to claim 1 wherein said 1,5-bis(3-aminophenoxy)-2,4-dihalogenobenzenes are a reaction product obtained by reacting a 1,2,4,5-tetrahalogenobenzene with 3-aminophenol in the presence of a dehydrohalogenating agent in an aprotic polar solvent and in the absence of an Ullmann reaction promotor.

* * * * *